(12) United States Patent
Hong et al.

(10) Patent No.: US 6,805,707 B1
(45) Date of Patent: Oct. 19, 2004

(54) STENT WITH IMPROVED RING AND LINK PATTERN

(75) Inventors: James Hong, San Jose, CA (US);
Sharon Segvich, Crown Point, IN (US);
E Tina Cheng, Union City, CA (US);
Napoleon Caliguiran, Union City, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 305 days.

(21) Appl. No.: 10/032,874

(22) Filed: Dec. 27, 2001

(51) Int. Cl.$^7$ ................................................ A61F 2/06
(52) U.S. Cl. ................................. 623/1.16; 606/108
(58) Field of Search .................... 623/1.1–1.2; 606/108, 606/191, 192, 194, 195, 198

(56) References Cited

U.S. PATENT DOCUMENTS

| | | | |
|---|---|---|---|
| 5,653,727 A | * | 8/1997 | Wiktor ...................... 623/1.15 |
| 5,957,949 A | * | 9/1999 | Leonhardt et al. ......... 623/1.24 |
| 6,033,433 A | * | 3/2000 | Ehr et al. .................. 623/1.16 |
| 6,066,168 A | * | 5/2000 | Lau et al. .................. 623/1.16 |
| 6,083,259 A | * | 7/2000 | Frantzen .................... 623/1.15 |
| 6,190,403 B1 | * | 2/2001 | Fischell et al. ............ 623/1.16 |
| 6,565,599 B1 | * | 5/2003 | Hong et al. ................ 623/1.15 |
| 6,607,554 B2 | * | 8/2003 | Dang et al. ................ 623/1.15 |
| 6,613,072 B2 | * | 9/2003 | Lau et al. .................. 623/1.11 |

FOREIGN PATENT DOCUMENTS

| WO | WO 02/00138 A2 | 1/2002 |
|---|---|---|
| WO | WO 02/24111 A2 | 3/2002 |

OTHER PUBLICATIONS

U.S. patent application Publication No. 2002/0042647 A1 to Jang published Apr. 11, 2002.
U.S. patent application Publication No. 2002/0045933 A1 to Jang published Apr. 18, 2002.
U.S. patent application Publication No. 2002/0045934 A1 to Jang published Apr. 18, 2002.
U.S. patent application Publication No. 2002/0045935 A1 to Jang published Apr. 18, 2002.
U.S. patent application Publication No. 2002/0052646 A1 to Fischell et al. published May 2, 2002.

* cited by examiner

*Primary Examiner*—Julian W. Woo
*Assistant Examiner*—Victor Nguyen
(74) *Attorney, Agent, or Firm*—Fulwider Patton Lee & Utecht, LLP

(57) ABSTRACT

The invention is directed to an expandable stent for implanting in a body lumen, such as a coronary artery, peripheral artery, or other body lumen. The invention provides for an intravascular stent having a plurality of cylindrical rings connected by links. The rings are defined by undulations of relatively large and relatively small amplitudes wherein bar arms extend between peaks and valleys and wherein selected bar arms are non-linear. The links connecting the cylindrical rings are non-linear.

29 Claims, 2 Drawing Sheets

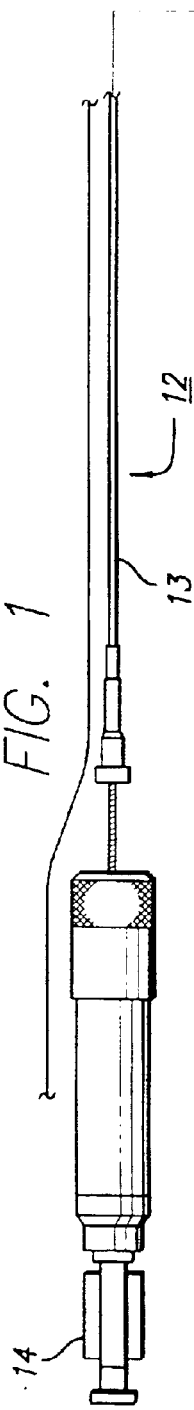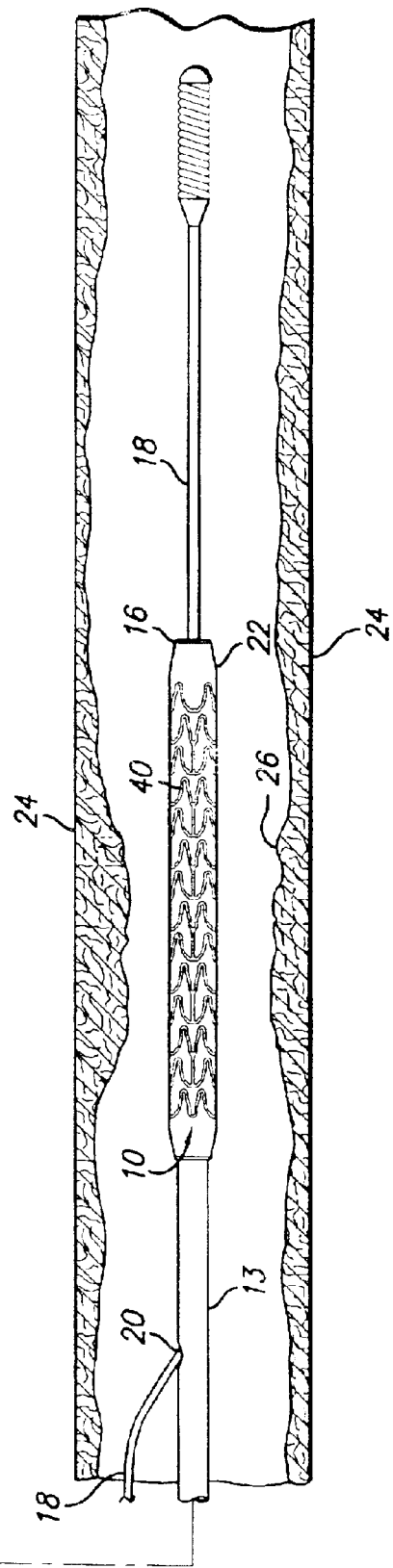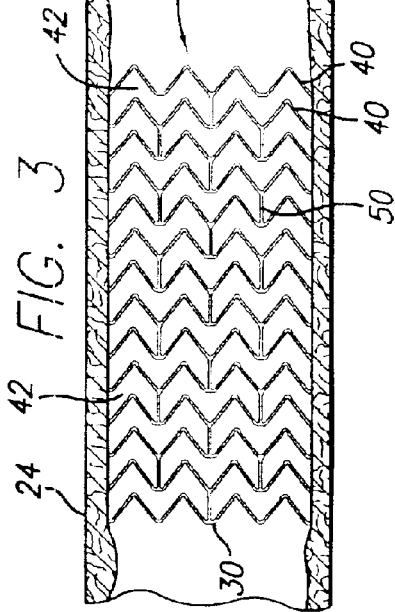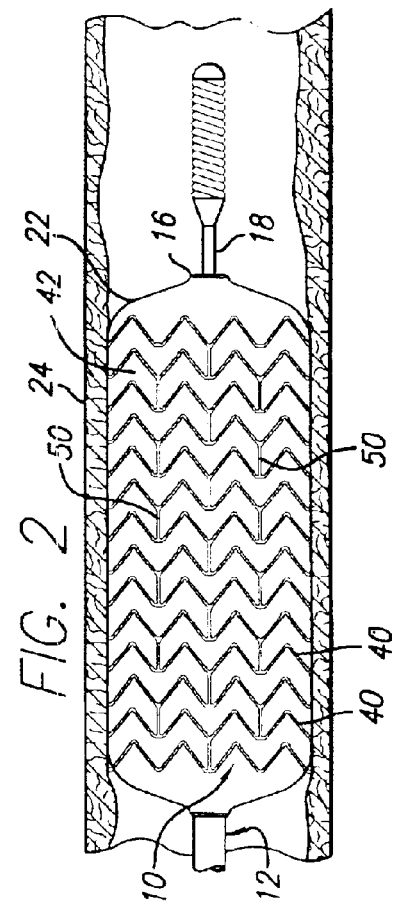

STENT WITH IMPROVED RING AND LINK PATTERN

BACKGROUND OF THE INVENTION

This invention relates to endoluminal prostheses such as vascular repair devices, and in particular intravascular stents, which are adapted to be implanted into a patient's body lumen, such as a blood vessel or coronary artery, to maintain the lumen's patency. Stents are particularly useful in the treatment of atherosclerotic stenosis and are most frequently used in connection with coronary angioplasty.

Stents are tubular, usually cylindrical devices which hold open a segment of blood vessel or other body lumen. They also are suitable to support and hold back a dissected arterial lining that can occlude the lumen. At present, numerous models of stents are marketed throughout the world. While some of these stents are flexible and have the appropriate, strength and rigidity needed to hold open a lumen such as a coronary artery, each stent design nonetheless represents a particular compromise among these properties as well as a number of additional competing parameters. What has been needed, and heretofore unavailable, is a stent which has a higher degree of flexibility both in its crimped as well as expanded state, as well as a reduced crimped profile, a larger expansion range and less unsupported surface area (USA), so that it can more readily be advanced through tortuous lumens and expanded, and yet have the mechanical strength to hold open the lumen or artery into which it is implanted and provide adequate vessel wall coverage.

The present invention provides a stent pattern which simultaneously provides for these advances over previously known stent configurations.

SUMMARY OF THE INVENTION

The present invention is directed to an endoluminal prosthesis, such as an intravascular stent, which is highly flexible along its longitudinal axis, both in its crimped state to facilitate delivery through tortuous body lumens as well as in its expanded state to minimize the potential for trauma upon deployment, but which is strong and stable enough radially in its expanded condition to maintain the patency of a body lumen when the stent is implanted therein. Additionally, its low profile while in its crimped state further enhances advanceability while its large expansion range and its minimal unsupported surface area (USA) more effectively provides support upon deployment.

The stent of the present invention includes a plurality of generally cylindrical elements, also known as rings, that are interconnected to form the stent. The stent typically is mounted on a balloon catheter if it is balloon expandable, or else it can be mounted on a catheter without a balloon if it is self-expanding.

Each of the cylindrical rings or elements has a proximal end and a distal end and a cylindrical outer wall surface that extends circumferentially between the proximal end and the distal end of the cylindrical ring. The cylindrical wall is defined by an undulating structure that extends proximally as well as distally. The structure consists of a series of peaks and valleys that are interconnected by bar arms. Undulations of both relatively large amplitude as well as of relatively smaller amplitude are present. In one of the preferred embodiments, the structure alternates between undulations of large amplitude and small amplitude such that each small amplitude undulation is sandwiched between two undulations of large amplitude. In another preferred embodiment, two small amplitude undulations are sandwiched between two undulations of the relatively larger amplitude. In the preferred embodiments at least one of the bar arms extending between an undulation of large amplitude and an undulation of relatively small amplitude is non-linear, preferably having an S-shape. The present invention further provides for the undulations in adjacent cylindrical rings to be either in phase of out of phase. At least one link extends between adjacent rings, wherein such link is preferably non-linear. The link may extend between a valley on one ring and a peak on the adjacent ring. Alternatively, the link may extend between the non-linear bar arm of one ring to the adjacent ring.

The number of peaks, valleys, links, and cylindrical rings can be varied as the application requires. The configuration of the rings and links provides the stent with a high degree of flexibility along the stent axis, both in its crimped state as well as its expanded state. Further, the combination of large and small amplitude undulations along with the non-linear bar arms allows the stent to be crimped to a very small profile while allowing for large expansion and a minimal unsupported surface area upon expansion.

Typically, a balloon expandable stent is made from a stainless steel alloy or similar material. The cylindrical rings of the stent are plastically deformed when expanded by the balloon.

The stent may be formed from a tube by laser cutting the pattern of cylindrical rings and flexible links in the tube. The stent also may be formed by laser cutting a flat metal sheet in the pattern of the cylindrical rings and links, and then rolling the pattern into the shape of the tubular stent and providing a longitudinal weld to form the stent.

Other features and advantages of the invention will become apparent from the following detailed description, taken in conjunction with the accompanying drawings, which illustrate, by way of example, the of the invention.

BRIEF DESCRIPTION OF THE DRAWINGS

FIG. 1 is an elevation view, partially in section, of a stent which is mounted on a rapid-exchange delivery catheter and positioned within an artery.

FIG. 2 is an elevation view, partially in section, similar to that shown in FIG. 1, wherein the stent is expanded within the artery so that the stent embeds within the arterial wall.

FIG. 3 is an elevation view, partially in section, showing the expanded stent implanted within the artery after withdrawal of the rapid-exchange delivery catheter.

DETAILED DESCRIPTION OF THE PREFERRED EMBODIMENTS

The present invention improves on existing endovascular prostheses, such as stents, by providing a novel ring and link pattern that serves to enhance flexibility, expandability and coverage. A significant aspect of the invention is the combination of undulations of various amplitudes to define the rings along with the inclusion of non-linear bar arms in selected portions of the rings. By additionally selecting the phasing of adjacent rings along with the use of non-linear links to link selected portions of adjacent rings, an improved stent configuration results. The stent can be crimped to a reduced crimped profile, and is very flexible while in its crimped state. More over the stent can be expanded to a larger expanded profile wherein it remains flexible and provides superior coverage.

Figure 4:
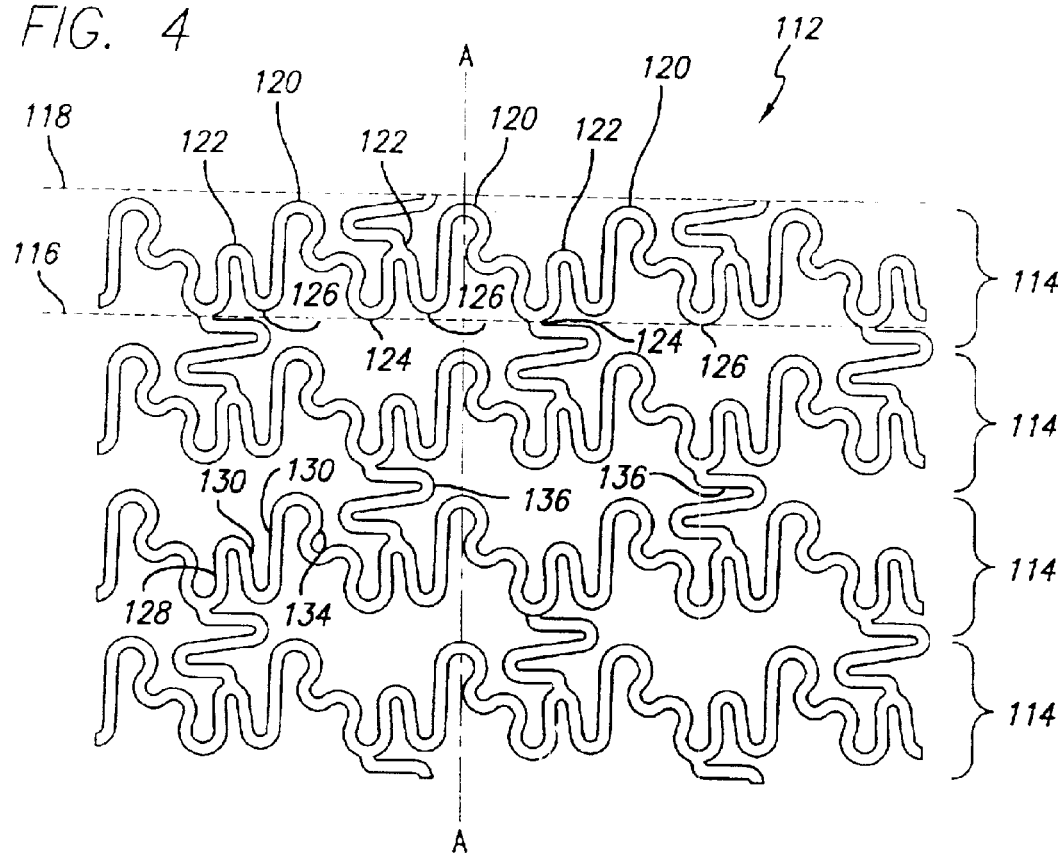
FIG. 4 is a flattened plan view of a stent pattern which illustrates a preferred configuration of the present invention.
Figure 5:
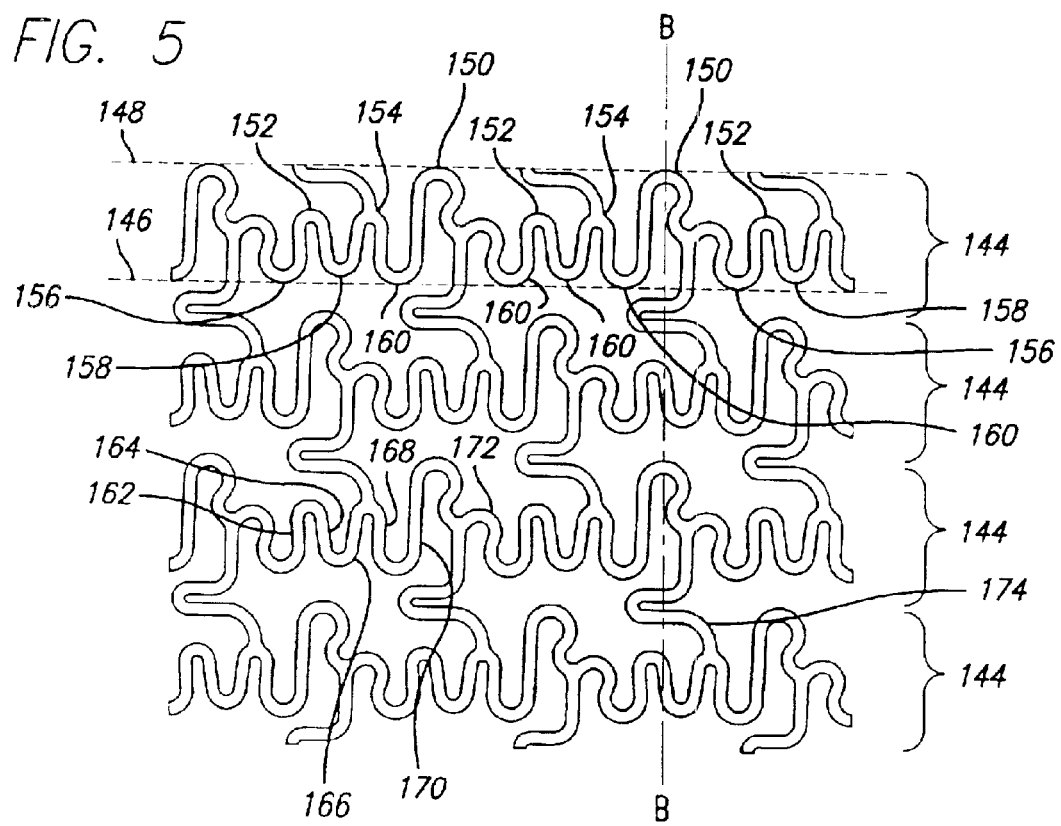
FIG. 5 is a flattened plan view of a stent pattern which illustrates another preferred configuration of the present invention

The present invention is the configuration of the material used to make an endoluminal prosthesis such as a stent. In other words, it is the stent pattern. Two preferred embodiments are depicted in FIGS. 4 and 5, while FIGS. 1–3 depict the use of stents in general.

FIGS. 1–3 can represent any balloon expandable stent 10 with which the various configurations of the present invention can be used. FIG. 1 depicts a stent 10 with interconnected cylindrical rings 40 mounted on a catheter assembly 12 which is used to deliver the stent 10 and implant it in a body lumen, such as a coronary artery, peripheral artery, or other vessel or lumen within the body. The catheter assembly includes a catheter shaft 13 which has a proximal end 14 and a distal end 16. The catheter assembly is configured to advance through the patient's vascular system by advancing over a guide wire by any of the well-known methods of an over-the-wire system (not shown) or a well-known rapid exchange catheter system, such as the one shown in FIG. 1. The stent 10 in FIGS. 1–3 conceptually represents any type of stent well-known in the art—one comprising a plurality of undulating cylindrical rings 40. An example of such a stent is the Tetra® stent, made by ACS.

Catheter assembly 12 as depicted in FIG. 1 includes an RX port 20 where the guide wire 18 exits the catheter. The distal end of the guide wire 18 exits the catheter distal end 16 so that the catheter advances along the guide wire on a section of the catheter between the RX (rapid exchange) port 20 and the catheter distal end 16. As is known in the art, the guide wire lumen which receives the guide wire is sized for receiving various diameter guide wires to suit a particular application. The stent is mounted on expandable member 22 (e.g., an angioplasty balloon) and is crimped tightly thereon, so that the stent and expandable member present a low profile diameter for delivery through the arteries.

As shown in FIG. 1, a partial cross-section of an artery 24 has a small amount of plaque that has been previously treated by angioplasty or other repair procedure. Stent 10 is used to repair a diseased or damaged arterial wall as shown in FIG. 1, or a dissection, or a flap, all of which are commonly found in the coronary arteries and other blood. The stent 10, and the stent of the present invention, also can be placed and implanted without any prior angioplasty.

In a typical procedure to implant stent 10, the guide wire 18 is advanced through the patient's vascular system by well-known methods, so that the distal end of the guide wire is advanced past the plaque or diseased area 26. Prior to implanting the stent, the cardiologist may wish to perform an angioplasty or other procedure (i.e., atherectomy) in order to open and remodel the vessel and the diseased area.

Thereafter, the stent delivery catheter assembly 12 is advanced over the guide wire so that the stent is positioned in the target area. The expandable member or balloon 22 is inflated by well-known means so that it expands radially outwardly and in turn expands the stent radially outwardly until the stent is apposed to the vessel wall. The expandable member is then deflated and the catheter withdrawn from the patient's vascular system. The guide wire typically is left in the lumen for post-dilatation procedures, if any, and subsequently is withdrawn from the patient's vascular system. As depicted in FIGS. 2 and 3, the balloon is fully inflated with the stent expanded and pressed against the vessel wall, and in FIG. 3, the implanted stent remains in the vessel after the balloon has been deflated and the catheter assembly and guide wire have been withdrawn from the patient.

The stent 10 holds open the artery after the catheter is withdrawn, as illustrated by FIG. 3. In the preferred embodiment, the stent is formed from a cylindrical tube with a constant wall thickness, so that the straight and undulating components of the stent are relatively flat in transverse cross-section, so that when the stent is expanded, its flat surface is pressed into the wall of the artery, and as a result does not interfere with the blood flow through the artery. After the stent is pressed into the wall of the artery, it eventually becomes covered with endothelial cell growth which further minimizes blood flow interference. The undulating portion of the stent provides good tacking characteristics to prevent stent movement within the artery. Because the cylindrical rings 40 are closely spaced at regular intervals, they provide uniform support for the wall of the artery, and consequently are well adapted to tack up and hold in place small flaps or dissections in the wall of the artery, as illustrated in FIGS. 2 and 3.

The stent 10 in FIG. 3 has fourteen cylindrical rings 40. The rings are connected by links 50. For the purpose of the present invention, the cylindrical rings 40 could also be connected by welds in a manner similar to the "S" series of stents presently sold by Medtronic Ave, Inc., or in some other manner.

FIGS. 4 and 5 depict two preferred configurations of the present invention. In FIG. 4, a portion of a stent 112 is shown in a flattened condition so that the pattern can be clearly viewed, even though the preferred embodiment is not made this way. The stent is typically formed from a tubular member, but it can be formed from a flat sheet such as the portion shown in FIG. 4 and rolled into a cylindrical configuration. Although welding flat sheets or rings is not a preferred method of manufacture, it can be used.

FIG. 4 represents four cylindrical rings 114 of stent 112. The stent can have any number of rings, and, depending upon the size of the rings, it is preferred that a stent of the present invention have more than the four rings 114 shown in FIG. 4. For reference, line A—A represents the longitudinal axis of a stent using the pattern depicted in FIG. 4. Each cylindrical/ring 114 has a cylindrical ring proximal end 116 and a cylindrical ring distal end 118. Each ring is defined by an undulating pattern wherein a repeating series of peaks 120,122 and valleys 124,126 are interconnected by various bar arms 128, 130, 132, 134. The peaks and valleys are sometimes generically referred to as crests. The selection of which crest is a peak and which crest is a valley is arbitrary and done for ease of reference. Those in the art will understand that, depending upon one's reference, a peak can be a valley, and vice versa. Moreover, those in the art will understand from context the meanings of peak, valley and crest. In this particular embodiment, the undulations are configured such that both relatively large amplitude undulations as well as relatively smaller amplitude undulations are present. More particularly, such large and small amplitude undulations alternate about the circumference of the ring. As is shown in FIG. 4, the crest 120 of each large amplitude undulation is sandwiched between the crests 122 of two small amplitude undulations. Conversely, the crest 122 of each small amplitude undulation is sandwiched between the crests 120 of two large amplitude undulations. Additionally, with the exception of one of the bar arms extending from the crest of each large amplitude undulation, all bar arms 128, 130, 132 are substantially linear and substantially parallel to one another. The one non-linear bar arm 134 extending from the crest of the large amplitude undulation is generally S-shaped and is diagonally oriented between the crest 120 of the large amplitude undulation and the valley 124 of the adjacent undulation.

Each of the rings 114 of the preferred embodiment shown in FIG. 4 is arranged such that the undulations of one ring are in phase with the undulations of the adjacent ring. In other words, the crests 120 of the large amplitude undulations in adjacent rings are all longitudinally aligned with one another. Similarly, the crests 122 of the small amplitude undulations in adjacent rings are all longitudinally aligned with one another. Links 136 serve to join adjacent rings to one another. In this preferred embodiment, two such links extend between each adjacent pair of rings and the links are non-linear. More particularly, the links each have a Z-shape and extend from the valley 124 that is joined to a crest 120 by the non-linear bar arm 134 to the crest 122 of a small amplitude undulation.

FIG. 5 represents four cylindrical rings 144 of stent 142. The stent can have any number of rings, and, depending upon the size of the rings, it is preferred that a stent of the present invention have more than the four rings 144 shown in FIG. 5. For reference, line B—B represents the longitudinal axis of a stent using the pattern depicted in FIG. 5. Each cylindrical ring 144 has a cylindrical ring proximal end 146 and a cylindrical ring distal end 148. Each ring is defined by an undulating pattern wherein a repeating series of peaks 150, 152, 154 and valleys 156, 158, 160 are interconnected by various bar arms 162, 164, 166, 168, 170 and 172. The peaks and valleys are sometimes generically referred to as crests. The selection of which crest is a peak and which crest is a valley is arbitrary and done for ease of reference. Those in the art will understand that, depending upon one's reference, a peak can be a valley, and vice versa. Moreover, those in the art will understand from context the meanings of peak, valley and crest. In this particular embodiment, the undulations are configured such that both relatively large amplitude undulations as well as relatively smaller amplitude undulations extend about the circumference of each ring. As is shown in FIG. 5, the crest 150 of each large amplitude undulation has two undulations of small amplitude, with crests 152, 154, positioned on each side. Conversely, the crests 152, 154 of adjacent small amplitude undulations are sandwiched between the crests 150 of two large amplitude undulations. Additionally, with the exception of one of the bar arms extending from the crest 150 of each large amplitude undulation, all bar arms 162, 164, 166, 168, 170 are substantially linear and substantially parallel to one another. The one non-linear bar arm 172 extending from the crest 150 of the large amplitude undulation is generally S-shaped and is diagonally oriented between the crest 150 of the large amplitude undulation and the valley 156 of the adjacent undulation.

Each of the rings 144 of the preferred embodiment shown in FIG. 5 is arranged such that the undulations are out-of-phase with one another. In other words, the crests 150 of the large amplitude undulations in adjacent rings are not longitudinally aligned with one another. As is visible along line B—B, the rings are aligned such that the crests 150 of large amplitude undulations alternate with the crests 152 of small amplitude undulations. Links 174 serve to join adjacent rings 144 to one another. In this preferred embodiment, two such links extend between each adjacent pair of rings and the links are non-linear. More particularly, the links each have a U-shape and extend from the non-linear diagonal bar arm 172 of one ring to the crest of a small amplitude undulation of an adjacent ring.

The stent of the present invention can be made in many ways. One method of making the stent is to cut a thin-walled tubular member, such as stainless steel tubing, to remove portions of the tubing in the desired pattern for the stent, leaving relatively untouched the portions of the metallic tubing which are to form the stent. In accordance with the invention, it is preferred to cut the tubing in the desired pattern by means of a computer controlled laser equipment, as is well known in the art Such methods are described in U.S. Pat. Nos. 5,759,192 and 5,780,807 to Saunders, which are incorporated herein by reference in their entirety.

The tubing may be made of suitable biocompatible material such as stainless steel or another metal alloy. The stainless steel tube may be alloy type: 316L SS, special chemistry per ASTM F138-92 or ASTM F139-92 grade 2. Special chemistry of type 316L per ASTM F138-92 or ASTM F139-92 stainless steel for surgical implants in weight percent.

| | |
|---|---|
| Carbon (C) | 0.03% max. |
| Manganese (Mn) | 2.00% max. |
| Phosphorous (P) | 0.025% max. |
| Sulphur (S) | 0.010% max. |
| Silicon (Si) | 0.75% max. |
| Chromium (Cr) | 17.00–19.00% |
| Nickel (Ni) | 13.00–15.50% |
| Molybdenum (Mo) | 2.00–3.00% |
| Nitrogen (N) | 0.10% max. |
| Copper (Cu) | 0.50% max. |
| Iron (Fe) | Balance |

The tubing is mounted in a rotatable collet fixture of a machine-controlled apparatus for positioning the tubing relative to a laser. According to machine-encoded instructions, the tubing is rotated and moved longitudinally relative to the laser, which is also machine controlled. The laser selectively removes the material from the tubing by ablation, thereby cutting a pattern into the tube.

The process of cutting a stent pattern into the tubing is automated, except for loading and unloading the length of tubing. In one example, a CNC opposing collet fixture for axial rotation of the length of tubing is used in conjunction with a CNC X/Y table to move the length of tubing axially relatively to a machine-controlled laser. The entire space between collets can be patterned using the $CO_2$ laser set-up of the foregoing example. The program for control of the apparatus is dependent on the particular configuration used and the pattern to be ablated in the coating.

Cutting a fine structure (e.g., a 0.0035 inch web width) requires minimal heat input and the ability to manipulate the tube with precision. It is also necessary to support the tube yet not allow the stent structure to distort during the cutting operation. In order to successfully achieve the desired end results, the entire system must be configured very carefully. The tubes for coronary stents are made typically of stainless steel with an outside diameter of 0.060 inch to 0.066 inch and a wall thickness of 0.002 inch to 0.004 inch. Dimensions for peripheral stents and other endoluminal prostheses may be different. These tubes are fixtured under a laser and positioned utilizing CNC equipment to generate a very intricate and precise pattern. Due to the thin wall and the small geometry of the stent pattern, it is necessary to have very precise control of the laser, its power level, the focused spot size, and the precise positioning of the laser cutting path.

Minimizing the heat input into the stent structure prevents thermal distortion, uncontrolled burn out of the metal, and metallurgical damage due to excessive heat, and thereby produces a smooth debris free cut. A Q-switched Nd-YAG, typically available from Quantronix of Hauppauge, N.Y., is utilized. The frequency is doubled to produce a green beam at 532 nanometers. Q-switching produces very short pulses (<100 nS) of high peak powers (kilowatts), low energy per pulse ($\leq 3$ mJ), at high pulse rates (up to 40 kHz). The frequency doubling of the beam from 1.06 microns to 0.532 microns allows the beam to be focused to a spot size that is 2 times smaller, therefore increasing the power density by a factor of 4 times. With all of these parameters, it is possible to make smooth, narrow cuts in the stainless tubes in very fine geometries without damaging the narrow struts that make up the stent structure. The system makes it possible to adjust the laser parameters to cut a narrow kerf width, which minimizes the heat input into the material.

The positioning of the tubular structure requires the use of precision CNC equipment, such as that manufactured and sold by Aerotech Corporation. In addition, a unique rotary mechanism has been provided that allows the computer program to be written as if the pattern were being cut from a flat sheet. This allows both circular and linear interpolation to be utilized in programming.

The optical system, which expands the original laser beam, delivers the beam through a viewing head and focuses the beam onto the surface of the tube. It incorporates a coaxial gas jet and nozzle that help to remove debris from the kerf and cool the region where the beam cuts and vaporizes the metal. It is also necessary to block the beam as it cuts through the top surface of the tube and prevent the beam, along with the molten metal and debris from the cut, from impinging on the opposite, inner surface of the tube.

In addition to the laser and the CNC positioning equipment, the optical delivery system includes: a beam expander to increase the laser beam diameter; a circular polarizer, typically in the form of a quarter wave plate, to eliminate polarization effects in metal cutting; provisions for a spatial filter; a binocular viewing head and focusing lens; and, a coaxial gas jet that provides for the introduction of a gas stream that surrounds the focused beam and is directed along the beam axis. The coaxial gas jet nozzle (0.018 inch I.D.) is centered around the focused beam with approximately 0.010 inch between the tip of the nozzle and the tubing. The jet is pressurized with oxygen at 20 psi and is directed at the tube with the focused laser beam exiting the tip of the nozzle (0.018 inch dia.). The oxygen reacts with the metal to assist in the cutting process, similar to oxy-acetylene cutting. The focused laser beam acts as an ignition source and controls the reaction of the oxygen with the metal. In this manner, it is possible to cut the material with a very fine, precise kerf. In order to prevent burning by the beam and/or molten slag on the far wall of the tube I.D., a stainless steel mandrel (approx. 0.034 inch dia.) is placed inside the tube and is allowed to roll on the bottom of the tube as the pattern is cut. This acts as a beam/debris block protecting the far wall I.D.

Alternatively, burning may be prevented by inserting a second tube inside the stent tube. The second tube has an opening to trap the excess energy in the beam, which is transmitted through the kerf and which collects the debris that is ejected from the laser cut kerf. A vacuum or positive pressure can be placed in this shielding tube to remove the collection of debris.

Another technique that could be utilized to remove the debris from the kerf and cool the surrounding material would be to use the inner beam blocking tube as an internal gas jet. By sealing one end of the tube and making a small hole in the side and placing it directly under the focused laser beam, gas pressure could be applied, creating a small jet that would force the debris out of the laser cut kerf from the inside out. This would eliminate any debris from forming or collecting on the inside of the stent structure. It would place all the debris on the outside. With the use of special protective coatings, the resultant debris could be easily removed.

In most cases, the gas utilized in the jets may be reactive or non-reactive (inert). In the case of reactive gas, oxygen or compressed air is used. Compressed air is used in this application since it offers more control of the material removed and reduces the thermal effects of the material itself. Inert gas such as argon, helium, or nitrogen can be used to eliminate any oxidation of the cut material. The result is a cut edge with no oxidation, but there is usually a tail of molten material that collects along the exit side of the gas jet that must be mechanically or chemically removed after the cutting operation.

The cutting process utilizing oxygen with the finely focused green beam results in a very narrow kerf (approx. 0.0005 inch) with the molten slag re-solidifying along the cut. This traps some scrap, thus requiring further processing. In order to remove the slag debris from the cut, it is necessary to soak the cut tube in a solution of HCL for approximately eight minutes at a temperature of approximately 55° C. Before it is soaked, the tube is placed in an alcohol and water bath and ultrasonically cleaned for approximately one minute. This removes the loose debris left from the cutting operation. After soaking, the tube is then ultrasonically cleaned in the heated HCL for one to four minutes, depending upon the wall thickness. To prevent cracking or breaking of the struts attached to the material left at the two ends of the stent pattern due to harmonic oscillations induced by the ultrasonic cleaner, a mandrel is placed down the center of the tube during the cleaning and scrap removal process. At the completion of this process, the stent structure is rinsed in water and is now ready for electropolishing.

The stents are preferably electrochemically polished in an acidic aqueous solution such as a solution of ELECTRO-GLO#300, sold by ELECTRO-GLO Co., Inc., Chicago, Ill., which is a mixture of sulfuric acid, carboxylic acid, phosphates, corrosion inhibitors and a biodegradable surface active agent. The bath temperature is maintained at about 110°–135° F. and the current density is about 0.4 to about 1.5 amps per in.$^2$. Cathode to anode area should be at least about two to one. The stents may be further treated if desired, for example by applying a biocompatible coating.

It will be apparent that both focused laser spot size and depth of focus can be controlled by selecting beam diameter and focal length for the focusing lens. It will be apparent that increasing laser beam diameter, or reducing lens focal length, reduces spot size at the cost of depth of field.

Direct laser cutting produces edges which are essentially perpendicular to the axis of the laser cutting beam, in contrast with chemical etching and the like which produce pattern edges which are angled. Hence, the laser cutting process essentially provides strut cross-sections, from cut-to-cut, which are square or rectangular, rather than trapezoidal. The struts have generally perpendicular edges formed by the laser cut. The resulting stent structure provides superior performance.

Other methods of forming the stent of the present invention can be used, such as chemical etching; electric discharge machining; laser cutting a flat sheet and rolling it into a cylinder; and the like, all of which are well known in the art at this time.

The stent of the present invention also can be made from metal alloys other than stainless steel, such as shape memory alloys. Shape memory alloys are well known and include, but are not limited to titanium, tantalum, nickel titanium and nickel/titanium/vanadium. Any of the superelastic or shape memory alloys can be formed into a tube and laser cut in order to form the pattern of the stent of the present invention. As is well known, the superelastic or shape memory alloys of the stent of the present invention can include the type known as thermoelastic martensitic transformation, or display stress-induced martensite. These types of alloys are well known in the art and need not be further described here.

Importantly, a stent formed of shape memory or superelastic alloys, whether the thermoelastic or the stress-induced martensite-type, can be delivered using a balloon catheter of the type described herein, or in the case of stress induced martensite, be delivered via a sheath catheter or a catheter without a balloon.

While the invention has been illustrated and described herein in terms of its use as an intravascular stent, it will be apparent to those skilled in the art that the stent can be used in other body lumens. Further, particular sizes and dimensions, the configuration of undulations, number of crowns per ring, materials used, and other features have been described herein and are provided as examples only. Other modifications and improvements may be made without departing from the scope of the invention. For example, the cylindrical rings can be octagonal, hexagonal, or some other polygon, thus possessing corners. Each ring is essentially a short tube, (or hoop or ring) whose length is preferably shorter than its diameter and which has a significant percentage of the tube surface removed. Other modifications could include the use of polymers in portions of the links and/or bar arms so that the stent would be more radiopaque. Alternatively, one could place electrical discontinuities in the stent to minimize the Faraday Cage effect and make the stent more visible under Magnetic Resonance Imaging.

While particular forms of the invention have been described and illustrated, it will also be a parent to those skilled in the art that various modifications can be made without departing from the spirit and the scope of the invention. Accordingly, it is not intended that the invention be limited except by the appended claims.

What is claimed is:

1. An intravascular stent for use in a body lumen, comprising:

a plurality of cylindrical rings aligned along a longitudinal axis, each ring having a) a first, delivery diameter, b) a second, implanted diameter, c) proximal and distal ends defining a generally cylindrical wall extending circumferentially between the proximal and distal ends, and (d) wherein such generally cylindrical wall is defined by a series of undulations of preselected amplitudes which are in turn defined by bar arms that interconnect peaks and valleys, wherein undulations of a relatively large amplitude are separated by at least one undulation of a relatively small amplitude and wherein at least one bar arm interconnecting a peak of each large amplitude undulation with a valley of a small amplitude undulation is non-linear; and at least one link connecting each cylindrical ring to an adjacent ring to form the stent.

2. The stent of claim 1, wherein said at least one non-linear bar arm has an S-shape.

3. The stent of claim 1, wherein only one bar arm interconnecting a peak of each large amplitude undulation with a valley of a small amplitude undulation is non-linear and wherein all other bar arms are linear.

4. The stent of claim 3, wherein said one non-linear bar arm has an S-shape.

5. The stent of claim 1, wherein said at least one link is non-linear.

6. The stent of claim 5, wherein said link has a Z-shape.

7. The stent of claim 5, wherein said link has a U-shape.

8. The stent of claim 1, wherein said series of undulations defining each cylindrical ring are in phase with respect to said series of undulations of each adjacent ring.

9. The stent of claim 1, wherein said series of undulations defining each cylindrical ring are out of phase with respect to said series of undulations of each adjacent ring.

10. The stent of claim 1, wherein said undulations of a relatively large amplitude are separated by a single undulation of a relatively small amplitude.

11. The stent of claim 10, wherein said at least one non-linear bar arm has an S-shape.

12. The stent of claim 10; wherein only one bar arm interconnecting a peak of each large amplitude undulation with a valley of a small amplitude undulation is non-linear and wherein all other bar arms are linear.

13. The stent of claim 12, wherein said one non-linear bar arm has an S-shape.

14. The stent of claim 10, wherein said series of undulations of each cylindrical ring are in phase with said series of undulations of each adjacent ring.

15. The stent of claim 10, wherein two links connect adjacent rings.

16. The stent of claim 15, wherein said links are non-linear.

17. The stent of claim 16, wherein said links each have a Z-shape.

18. The stent of claim 16, wherein said links extend between a peak and a valley of adjacent rings.

19. The stent of claim 1, wherein said undulations of relatively large amplitude are separated by two undulations of a relatively small amplitude.

20. The stent of claim 19, wherein said at least one non-linear bar arm has an S-shape.

21. The stent of claim 19, wherein only one bar arm interconnecting a peak of each large amplitude undulation with a valley of a small amplitude undulation is non-linear and wherein all other bar arms are linear.

22. The stent of claim 21, wherein said one non-linear bar arm has an S-shape.

23. The stent of claim 19, wherein said series of undulations of each cylindrical ring are out of phase with respect to said series of undulations of each adjacent ring.

24. The stent of claim 19, wherein two links connect adjacent rings.

25. The stent of claim 24, wherein said links are non-linear.

26. The stent of claim 25, wherein said links each have a U-shape.

27. The stent of claim 25, wherein each of said links extend from a non-linear bar arm of a cylindrical ring to an adjacent cylindrical ring.

28. The stent of claim 27, wherein each of said links extends from only one non-linear bar arm.

29. An intravascular stent for use in a body lumen, comprising:

a plurality of cylindrical rings aligned along a longitudinal axis, each ring having a) a first, delivery diameter, b) a second, implanted diameter, c) proximal and distal ends defining a generally cylindrical wall extending circumferentially between the proximal and distal ends, and d) wherein such generally cylindrical wall is defined by a series of undulations of preselected amplitudes which are in turn defined by bar arms that interconnect peaks and valleys, wherein undulations of a relatively large amplitude are separated by at least one undulation of a relatively small amplitude and wherein at least one bar arm interconnecting a peak of each large amplitude undulation with a valley of a small undulation is non-linear; and at least one link connecting each cylindrical ring to an adjacent ring to form the stent;

the small amplitude undulation having a peak with a curved crest;

the peak of the large amplitude undulation being connected to a linear bar arm on one side and the non-linear bar arm extending to the small amplitude undulation on the other side.

* * * * *

UNITED STATES PATENT AND TRADEMARK OFFICE
CERTIFICATE OF CORRECTION

PATENT NO. : 6,805,707 B1
DATED : October 19, 2004
INVENTOR(S) : James Hong et al.

It is certified that error appears in the above-identified patent and that said Letters Patent is hereby corrected as shown below:

Column 4,
Line 60, delete "cylindrical/ring" and insert -- cylindrical ring --.

Column 10,
Line 23, delete "a parent" and insert -- apparent --.

Signed and Sealed this

First Day of March, 2005

JON W. DUDAS
*Director of the United States Patent and Trademark Office*